United States Patent
Buess

(10) Patent No.: US 8,352,206 B2
(45) Date of Patent: Jan. 8, 2013

(54) METHOD FOR THE SIGNAL LINEARIZATION OF A GAS SENSOR OUTPUT SIGNAL

(75) Inventor: Christian Buess, Horgen (CH)

(73) Assignee: ndd Medizintechnik AG, Zurick (CH)

( * ) Notice: Subject to any disclaimer, the term of this patent is extended or adjusted under 35 U.S.C. 154(b) by 478 days.

(21) Appl. No.: 12/635,200

(22) Filed: Dec. 10, 2009

(65) Prior Publication Data

US 2011/0119012 A1    May 19, 2011

(30) Foreign Application Priority Data

Nov. 17, 2009  (EP) .................................... 09014380

(51) Int. Cl.
*G01D 18/00* (2006.01)
(52) U.S. Cl. ......................................................... 702/86
(58) Field of Classification Search .................... 702/86; 700/284, 282; 600/532
See application file for complete search history.

(56) References Cited

U.S. PATENT DOCUMENTS

| | | | |
|---|---|---|---|
| 7,809,473 B2 * | 10/2010 | Shajii et al. | 700/282 |
| 2004/0158411 A1 | 8/2004 | Morrow et al. | |
| 2007/0191726 A1 * | 8/2007 | Harnoncourt et al. | 600/532 |

FOREIGN PATENT DOCUMENTS

| EP | 0653919 | 5/1995 |
|---|---|---|
| EP | 1764035 | 3/2007 |

* cited by examiner

*Primary Examiner* — Jonathan C Teixeira Moffat
*Assistant Examiner* — Xiuquin Sun
(74) *Attorney, Agent, or Firm* — Dilworth & Barrese, LLP.

(57) ABSTRACT

The invention describes a method that is used to determine the linearization curve of a sensor for specific gas components by combining this sensor with an ultrasonic molar mass sensor. The described method uses the fact that the molar mass sensor exhibits a completely linear response when two gas compositions of differing molar mass values are mixed. Using this feature a non linear-response of a sensor for specific gas components can be determined and a linearization curve can be computed.

11 Claims, 1 Drawing Sheet

METHOD FOR THE SIGNAL LINEARIZATION OF A GAS SENSOR OUTPUT SIGNAL

BACKGROUND OF THE INVENTION

The invention relates to a method for the signal linearization of a gas sensor output signal.

The linearization of gas sensor output signals is used in many different areas. As an example this description uses an application in the medical field, specifically the use of gas sensors in the measurement of in- and exhaled gases.

In lung function diagnostics measurement of the diffusing capacity using carbon monoxide (DLCO) is a method that is based on the measurement of specific gas concentrations during in- and exhalation of a test gas by the patient. Commonly used DLCO gas mixes for this test type consist of 0.3% Carbon Monoxide (CO), 10% Helium (He), and 21% Oxygen ($O_2$) with balance Nitrogen ($N_2$). When a test is performed in a patient, this test gas is first inhaled by the patient, and then the patient performs a 10 seconds breath hold, followed by a normal exhalation. During the breath hold Helium is diluted, and the CO is diluted and absorbed into the blood. In order to compute the diffusing capacity the dilution of Helium and the absorption of CO have to be measured with high accuracy. For that purpose the inspiratory gas concentrations as well as the expiratory gas concentrations of Helium and CO must be measured using appropriate gas sensors. Normally separate gas sensors for CO and Helium are used. Since these gas sensors are often non-linear, (i.e. a linear increase in gas concentration is not equal to a linear increase in output signal of the sensor); the output of the sensor signal must be linearized. This is normally achieved by determining the non-linearity of the sensor during production. A sensor-individual or a standardized linearization is then applied to the output signal when the sensor is in use. This method, however, does not allow checking the linearization when the sensor is in use and this method can also not take into account changing characteristics of the gas sensor during its life time.

Currently linearization of an output signal of a gas sensor is normally performed using one of the following methods:

1. A fixed linearization curve is determined during the development of the gas sensor. That linearization curve is then applied to all gas sensors of that type. This method does not take into account that the characteristics of the gas sensor non-linearity may be different between individual gas sensors. It also does not take into account that the characteristics may change over time.
2. The linearization curve is determined on an individual base for each gas sensor that is produced. The linearization curve is determined using defined gas mixtures. This method does not take into account that the characteristics of the gas sensor may change over time.
3. The linearization curve of the gas sensor is determined during operation of the device using defined gas mixtures. In order to determine a linearization curve, normally at least three gas mixtures are used, i.e. gas mixtures at 0%, 50% and 100% of the output range of the gas sensor. When the sensor is in use this method requires at least one additional precision gas mix and therefore additional hardware.

As described above, the gas sensor linearization according to the prior art shows one or more disadvantages.

SUMMARY OF THE INVENTION

The present invention describes a method that allows simple linearization of a gas sensor output signal using an additional molar mass sensor.

This method can be used e.g. in a device for lung function diagnostic measurement.

The described method for gas sensor signal linearization can also be used in other fields than lung function testing. It can be applied for medical or non-medical applications.

The object of the invention is to show an easier method for the signal linearization of a gas sensor output signal which does not show the disadvantages of the state of the art.

This objective is solved by the method for the signal linearization of a gas sensor output signal with the steps described herein.

Preferred aspects of the invention can be taken from the description herein.

The invention can be used to automatically determine the linearization curve of a specific gas sensor.

BRIEF DESCRIPTION OF THE DRAWINGS

Further details and advantages of the invention will be explained in detail by means of the embodiment illustrated in the drawing in which.

DESCRIPTION OF THE PREFERRED EMBODIMENTS

Figure 1:
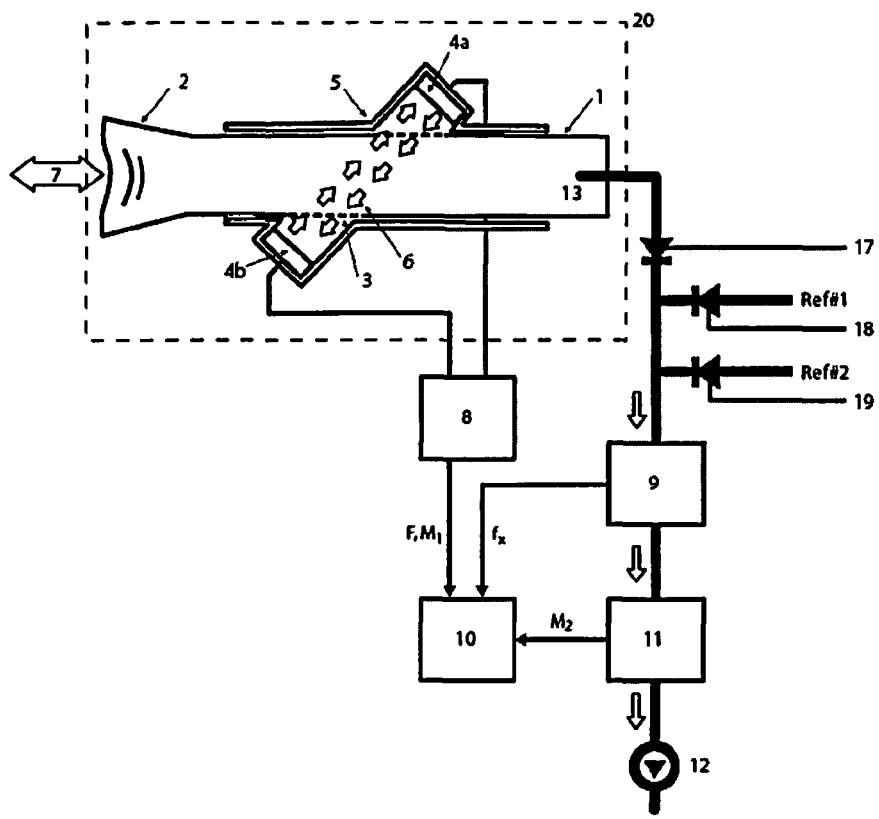
FIG. 1: shows a block diagram of a subsystem that can be used to determine diffusion capacity of the lung using Carbon Monoxide (DLCO)

The invention presented can be used to automatically determine the linearization curve of a specific gas sensor. FIG. 1 shows a block diagram of a sub-system that can be used to determine diffusing capacity of the lung using Carbon Monoxide (DLCO). The sub-system consists of an ultrasonic flow sensor 20 and an ultrasonic side-stream molar mass sensor 11 and a separate CO gas sensor 9. The operation of an ultrasonic flow meter is described in many publications (see EP 0 597 060 B1, EP 0 653 919 B1, Ch. Buess, P. Pietsch, W. Guggenbühl, E. A. Koller, "Design and construction of a pulsed ultrasonic air flowmeter", IEEE Trans. Biomed. Eng., 33(8):768-774, August 1986). The flow sensor consists of two ultrasonic transducers 4a, 4b mounted on opposite sides of the gas flow 7, an appropriate case 5 and an exchangeable breathing tube 1 with attached mouth piece 2. The gas flow velocity is determined in a signal processing unit 8 using the transit-times (time-of-flight) of ultrasonic pulse trains 6 transmitted in up- and downstream direction of the gas flow. The pulse trains are transmitted and received by the ultrasonic transducers. The pulse trains travel along the sound transmission path through ultrasonically permeable parts (3, e.g. meshes, filters etc.) of the flow tube. Flow velocity is determined using the following equation:

$$F = k \frac{t_1 - t_2}{t_1 \cdot t_2},$$

where F is the velocity of the gas flow, $t_1$ and $t_2$ represent the transit-times in up- and downstream direction, and k is a constant that depends on the mechanical dimensions of the flow sensor.

At the end of the breathing tube 1 a small fraction of the main-stream flow is fed to a side-stream system over a gas sampling tip 13. By using a gas pump 12 the side-stream flow passes a specific gas for CO 9 and an additional side-stream ultrasonic molar mass sensor 11. The side-stream gas flow tubing consists of normal plastic tubing, but it may also contain special tubing that equilibrates water vapor so that the side stream gas flow exhibits a constant humidity (i.e. constant partial pressure of water vapor). Alternative gas sampling arrangements for the side-stream flow have been shown in EP 1 764 036 B1.

The arrangement and the type of gas sensors may vary depending on the type of application. The molar mass gas sensor and the specific gas sensor that requires linearization may be arranged in series or also in parallel, precedence of the sensors may also vary depending on the application. It is mandatory, however, that the exact same gas passes both the specific gas sensor and the molar mass sensor. The molar mass sensor is a non-specific gas sensor since it can only measure the molar mass of a gas mixture, but it cannot differentiate between different gas components.

Other examples for specific gas sensors used in medical applications that require linearization are sensors for Helium, $CH_4$ or $CO_2$.

In addition to flow F the processing unit of the ultrasonic flow sensor 8 can also determine molar mass $M_1$ of the gas within the flow sensor. Molar mass is normally determined using the following equation:

$$M = k \cdot \kappa \cdot R \cdot T \cdot \left(\frac{t_1 \cdot t_2}{t_1 + t_2}\right)^2,$$

where M is the molar mass, T is the mean temperature along the sound transmission path, R is the gas constant, $\kappa$ is the relation of the specific heat capacities $c_p/c_v$ of the gas, k is a constant that depends on the mechanical dimensions of the sensor, and $t_1$ and $t_2$ represent the transit-times (see EP 0 653 919 B1). Temperature T can be determined by one or several temperature measurements along the sound transmission path; it can be determined by a combination of a temperature measurement and a mathematical model; or it can be a constant value.

The side-stream molar mass sensor 11 uses the same measurement principle to determine molar mass in the side-stream $M_2$. The signals of main-stream flow and molar mass F, $M_1$, side-stream molar mass $M_2$ and the signal of the specific gas sensor 9, $f_x$ are all fed to a computational unit 10.

An arrangement of valves is used to control the type of gas that is fed to the gas sensor 9 and the molar mass sensor 11 in the side-stream flow. Valve 17 activates the side-stream flow from the gas sampling tip 13, valve 18 activates gas from Ref#1, and valve 19 activates gas from Ref#2. Ref#1 and Ref#2 are two gas compositions that are used to determine the response of the specific gas sensor 9. In order to perform a linearization of the specific gas sensor 9 the two reference gases (Ref#1 and Ref#2) must have differing molar mass values. The two reference gases must also contain differing concentrations of the gas measured by the specific gas sensor 9.

In the following it is assumed that the reference gas Ref#1 contains 0% and Ref#2 100% of the gas measured by the specific gas sensor. In the case of a system for DLCO measurement Ref#1 could be room air (0% CO, 0% Helium, 21% Oxygen with balance Nitrogen); Ref#2 could be the DLCO test gas (0.3% CO, 10% Helium, 21% Oxygen with balance Nitrogen).

Figure 2:
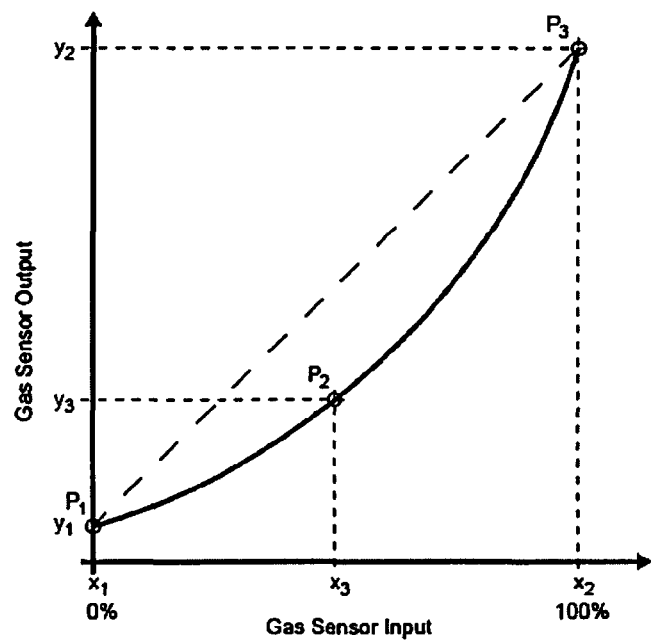
FIG. 2: a diagram showing the gas sensor output over the gas sensor input.

A three point linearization of the gas sensor output signal can be performed by executing the following steps:

1. Only Ref#1 valve 18 is activated: In this case only reference gas Ref#1 is passing through the molar mass and gas sensor. The offset $y_1$ of the specific gas sensor can be determined (output of gas sensor at 0%, see FIG. 2).
2. Only Ref#2 valve 19 is activated: In this case only reference gas Ref#2 is passing through the molar mass and gas sensor. The output value $y_2$ of the specific gas sensor can be determined (output of gas sensor at 100%, see FIG. 2).
3. Valves Ref#1 18 and Ref#2 19 are activated simultaneously: In this case a mixture of reference gases Ref#1 and Ref#2 is passing molar mass and specific gas sensor. Since the molar mass sensor exhibits a linear response the mixture ratio and hence $x_3$ can be determined using the output of the molar mass sensor. The output value $y_3$ of the specific gas sensor can be determined (output of the gas sensor at $x_3$%, see FIG. 2).

Having performed these three steps the points P1, P2 and P3 (FIG. 2) can be determined. By performing a polynomial (or similar) fit a linearization function for the gas sensor output signal can be determined.

If one or both valves for reference gases Ref#1 and Ref#2 can be controlled linearly several points between Ref#1 and Ref#2 can be produced and more data points along the linearization curve can be determined. Interpolation or regression methods can then be used to determine the linearization curve for the specific gas sensor.

The described method uses the fact that the molar mass sensor exhibits a completely linear response when two gas compositions of differing molar mass values are mixed. Using this feature a non linear-response of a sensor for specific gas components can be determined and a linearization curve can be computed.

The invention claimed is:

1. Method for the signal linearization of a gas sensor output signal in a device consisting of a computational unit, an ultrasonic molar mass sensor in combination with a gas sensor for a specific gas component where the linearity, defined as the input to output response characteristic, of the gas sensor is determined using two reference gases (Ref#1 and Ref#2) that have differing molar mass values and contain differing gas concentrations at the low end and at the high end of the measurement range of the gas sensor, including the following steps:

measuring the output value of the molar mass sensor and the output of the gas sensor at least at three gas mixture values of the two reference gases (Ref#1 and Ref#2) to generate measured data points associated with said gas mixture values;

computing by the computational unit the percentage by which the reference gases (Ref#1 and Ref#2) are mixed based on the output of the molar mass sensor;

determining by the computational unit a linearization curve based on the relation between the computed percentage by which the reference gases (Ref#1 and Ref#2) are mixed and the measured data points of the gas sensor output; and determining by the computational unit an effective linearization curve of the gas sensor by interpolation or regression between the measured data points of the linearization curve.

2. Method according to claim 1, wherein two reference gases (Ref#1 and Ref#2) are used and where three gas mixtures are created by using two on/off valves so that the three gas mixtures are the first reference gas (Ref#1), the second reference gas (Ref#2) and an approximately 50% mixture of the two reference gases (Ref#1 and Ref#2).

3. Method according to claim 2, wherein the linearization curve is determined by a polynomial or similar curve fit between the measured data points.

4. Method according to claim 3, wherein the linearization method is used for medical or industrial application.

5. Method according to claim 4, wherein the linearization method is performed automatically prior to each measurement cycle or test or at fixed time intervals between tests or measurements.

6. Method according to claim 5, wherein an additional pressure sensor is used to correct the output signal of the gas sensor.

7. Method according to claim 1, wherein two reference gases (Ref#1 and Ref#2) are used and several gas mixtures of the two reference gases (Ref#1 and Ref#2) are created using one on/off valve in combination with a linearly controlled valve, or by using two linearly controlled valves.

8. Method according to claim 7, wherein the linearization curve is determined by a polynomial or similar curve fit between the measured data points.

9. Method according to claim 8, wherein the linearization method is used for medical or industrial application.

10. Method according to claim 9, wherein the linearization method is performed automatically prior to each measurement cycle or test or at fixed time intervals between tests or measurements.

11. Method according to claim 10, wherein an additional pressure sensor is used to correct the output signal of the gas sensor.

* * * * *